US011177442B1

(12) United States Patent
Luo et al.

(10) Patent No.: US 11,177,442 B1
(45) Date of Patent: Nov. 16, 2021

(54) THERMALLY ACTIVATED DELAYED FLUORESCENCE MATERIAL AND ORGANIC LIGHT EMITTING DIODE DISPLAY DEVICE

(71) Applicant: WUHAN CHINA STAR OPTOELECTRONICS SEMICONDUCTOR DISPLAY TECHNOLOGY CO., LTD., Hubei (CN)

(72) Inventors: Jiajia Luo, Hubei (CN); Qu Zhang, Hubei (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 298 days.

(21) Appl. No.: 16/498,119

(22) PCT Filed: May 15, 2019

(86) PCT No.: PCT/CN2019/086994
§ 371 (c)(1),
(2) Date: Sep. 26, 2019

(87) PCT Pub. No.: WO2020/191894
PCT Pub. Date: Oct. 1, 2020

(30) Foreign Application Priority Data

Mar. 26, 2019 (CN) ........................ 201910234700.X

(51) Int. Cl.
*C09K 11/06* (2006.01)
*C07D 401/14* (2006.01)
(Continued)

(52) U.S. Cl.
CPC ........ *H01L 51/0067* (2013.01); *C07D 401/14* (2013.01); *C09K 11/06* (2013.01);
(Continued)

(58) Field of Classification Search
None
See application file for complete search history.

(56) References Cited

U.S. PATENT DOCUMENTS

2004/0242886 A1* 12/2004 Gupta .................. C07D 237/12
546/117

FOREIGN PATENT DOCUMENTS

CN 108658940 A 10/2018

OTHER PUBLICATIONS

Jurgensen, N. Chem. Mater. 2017, 29, 9154-9161.*
(Continued)

*Primary Examiner* — Clinton A Brooks

(57) ABSTRACT

A thermally activated delayed fluorescent material includes a structural formula (I) as follows:

(I)

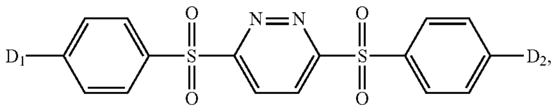

and D1 and D2 are different electron donors. In addition, an organic light emitting diode display device includes an anode, a cathode, and an organic functional layer disposed between the anode and the cathode. The organic functional layer includes a thermally activated delayed fluorescent
(Continued)

material, and the thermally activated delayed fluorescent material includes a structural formula (I).

14 Claims, 1 Drawing Sheet

(51) Int. Cl.
*H01L 51/00* (2006.01)
*H01L 51/50* (2006.01)
(52) U.S. Cl.
CPC .. *H01L 51/0072* (2013.01); *C09K 2211/1007* (2013.01); *C09K 2211/1014* (2013.01); *C09K 2211/1022* (2013.01); *H01L 51/5012* (2013.01); *H01L 51/5072* (2013.01)

(56) References Cited

OTHER PUBLICATIONS

Oleksandr Bezvikonnyl, et al; "Effect of donor substituents on thermally activated fluorescence of diphenylsulfone derivatives", Journal of Luminescence, vol. 206, Feb. 2019; **Abstract Only****.

* cited by examiner

THERMALLY ACTIVATED DELAYED FLUORESCENCE MATERIAL AND ORGANIC LIGHT EMITTING DIODE DISPLAY DEVICE

BACKGROUND OF INVENTION

Field of Invention

The present invention relates to a field of organic electroluminescent materials, and more particularly to a thermally activated delayed fluorescence material and an organic light emitting diode display device.

Description of Prior Art

Dominant guest luminescent materials are critical for affecting luminescent efficiency of organic light emitting diode (OLED) display devices. Generally, the luminescent guest materials used in OLED display devices are fluorescence materials. Generally, a ratio of singlet excitons to triplet excitons in the OLED display devices is 1:3, so an internal quantum efficiency (IQE) of the OLED display devices is merely 25%. Therefore, application of fluorescent electroluminescent devices is greatly limited. The phosphorescent heavy-metal complexes can achieve 100% IQE by using singlet and triplet excitons simultaneously due to the spin-orbit coupling of heavy atoms. However, the used heavy-metals are precious metals, such as iridium (Ir) or platinum (Pt). The phosphorescent heavy-metal complexes must be improved in terms of blue light materials. In addition, pure organic thermally activated delayed fluorescence materials have a lowest single-triplet level difference (ΔEST) which is relatively less than ever before, so that triplet excitons can be transformed to a singlet state by reverse intersystem crossing (RISC) and then are illuminated when jumping to a ground state transition by radiation. Therefore, single and triplet excitons can be simultaneously used and achieve 100% IQE.

As for the thermally activated delayed fluorescence materials, a high reaction rate constant of reverse intersystem enthalpy constant ($k_{RISC}$) and a high photoluminescence quantum yield (PLQY) are necessary for fabricating OLED display devices having high luminescent efficiency. Currently, the thermally activated delayed fluorescence materials with the above features are still relatively lacking as compared with heavy metal complexes.

SUMMARY OF INVENTION

A novel deep blue thermally activated delayed fluorescent material having high thermal stability and a high ratio of thermally activated delayed fluorescent materials to photoluminescence quantum yield to solve the problems in the prior art.

A thermally activated delayed fluorescent material includes a structural formula (I) as follows:

(I)

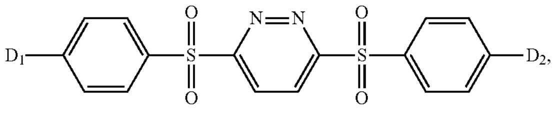

and D1 and D2 are different electron donors.

In one embodiment, the D1 includes one of following chemical structural formulas:

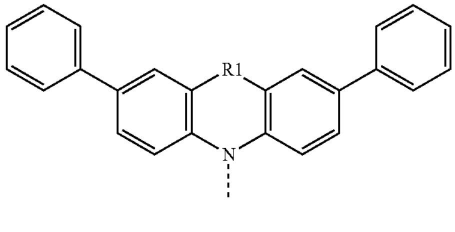
, and R1 is selected one from an oxygen or a C1-C3 alkyl group;

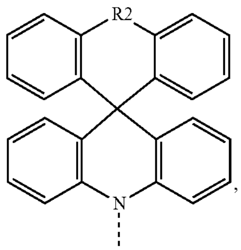
, and the R2 selected one from a C1-C3 alkyl or a silane group;

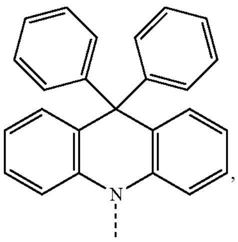
, or

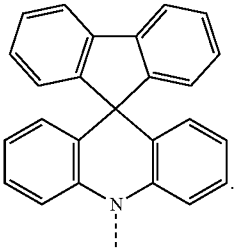
.

In one embodiment, the D1 is selected one from the group consisting of

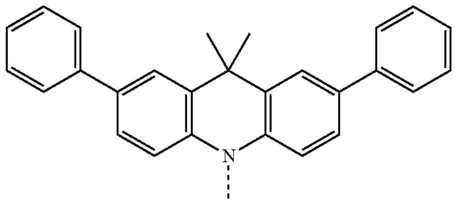
,

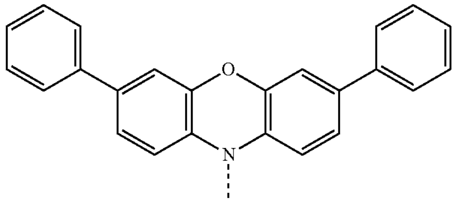
,

-continued

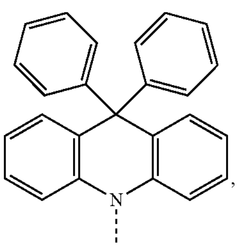
,
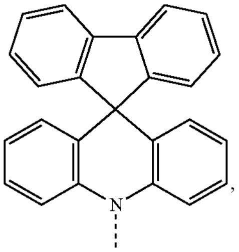
,
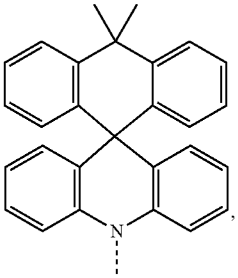
, and
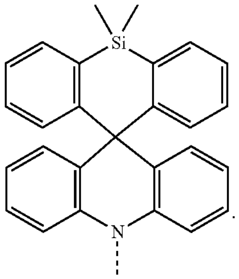
.

In one embodiment, and the D2 has a structural formula (I) as follows:

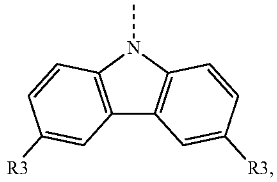
, and the R3 is selected one from a hydrogen, a C1-C4 alkyl, an alkoxy, or an aryl.

In one embodiment, the D2 is selected one from the group consisting of

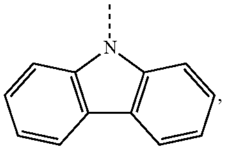
,
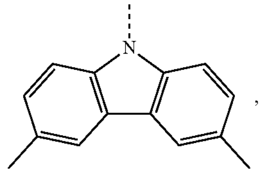
,
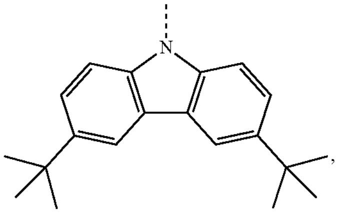
,
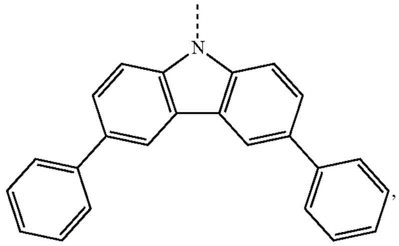
, and

-continued

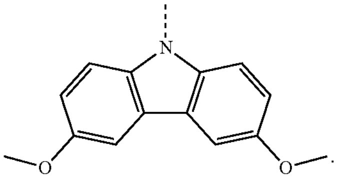
.

An organic light emitting diode display device includes an anode, a cathode, and an organic functional layer disposed between the anode and the cathode, and the organic functional layer includes a thermally activated delayed fluorescent material, and the thermally activated delayed fluorescent material includes a structural formula (I) as follows:

(I)

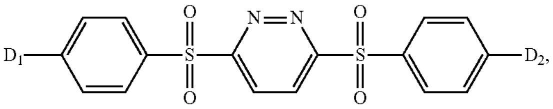
, and the D1 is selected one from the group consisting of

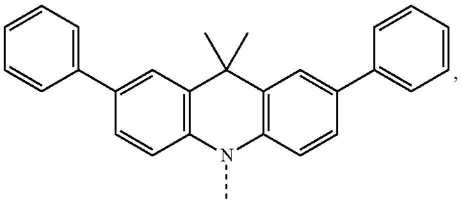
,
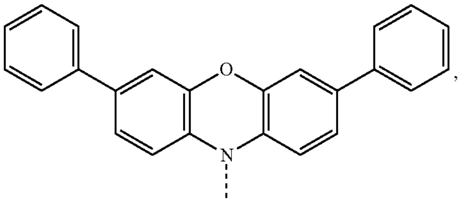
,
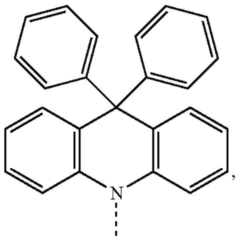
,
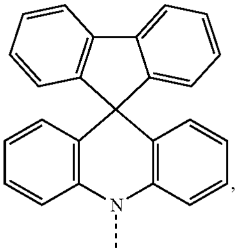
,

-continued

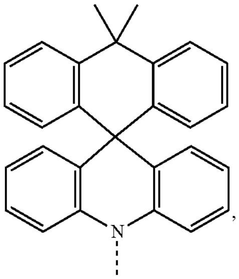

, and

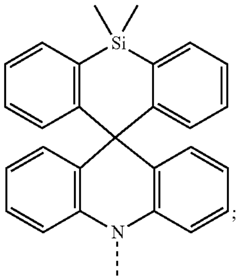

;

and

D2 is selected one from the group consisting of

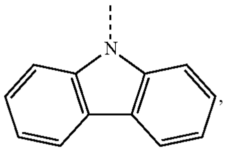

,

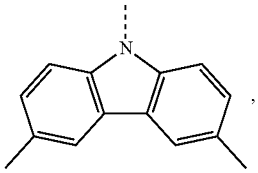

,

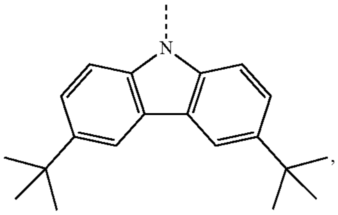

,

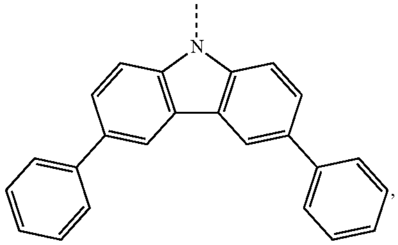

, and

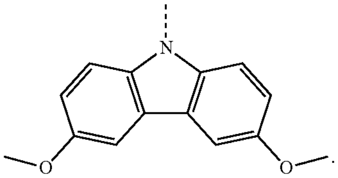

.

In one embodiment, and the thermally activated delayed fluorescent material is a fluorescent host material used in the organic light emitting diode display device.

In one embodiment, and the thermally activated delayed fluorescent material is an electron transporting material used in the organic light emitting diode display device.

A thermally activated delayed fluorescent material includes a structural formula (I) as follows:

(I)

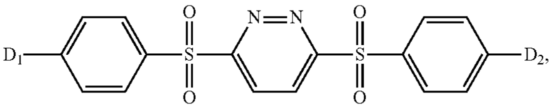

and D1 and D2 are different electron donors, and the D1 includes one of following chemical structural formulas:

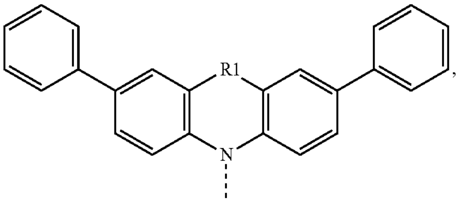

and R1 is selected one from an oxygen or a C1-C3 alkyl group;

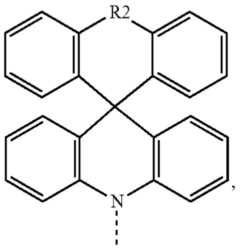

and the R2 selected one from a C1-C3 alkyl or a silane group;

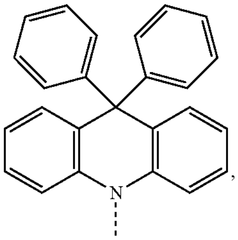

, or

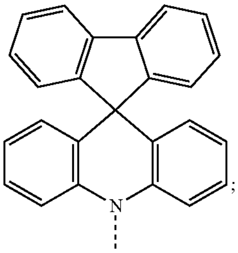

;

and the D2 has a structural formula (I) as follows:

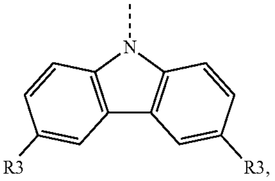

and the R3 is selected one from a hydrogen, a C1-C4 alkyl, an alkoxy, or an aryl.

In one embodiment, and the D1 is selected One from the group consisting of 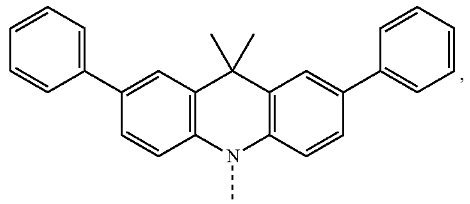,

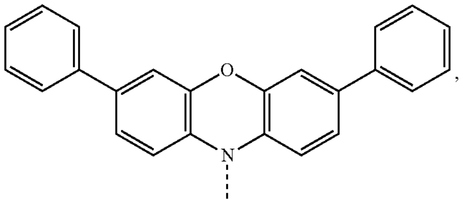,

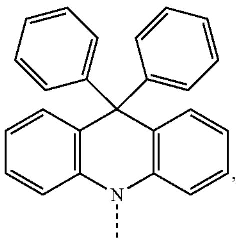, 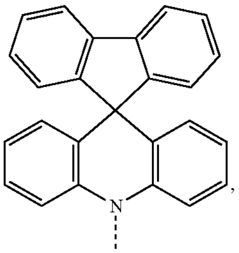,

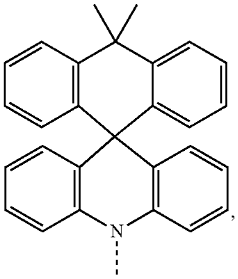, and 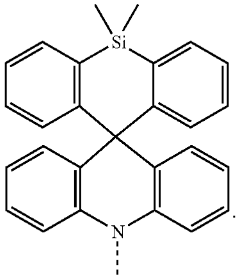.

In one embodiment, and the D2 is selected one from the group consisting of 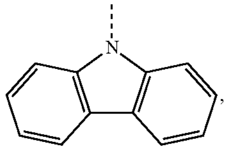, 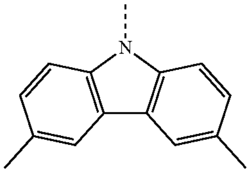,

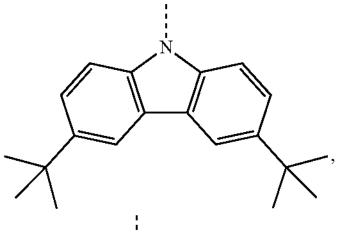,

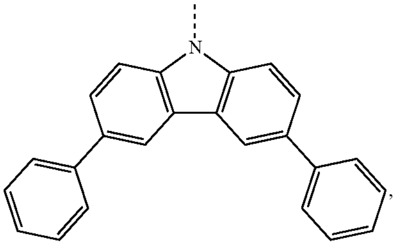, and

-continued

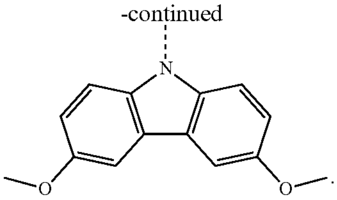.

In one embodiment, the organic functional layer includes a thermally activated delayed fluorescent material.

In one embodiment, the thermally activated delayed fluorescent material is a fluorescent host material used in the organic light emitting diode display device.

In one embodiment, the thermally activated delayed fluorescent material is an electron transporting material used in the organic light emitting diode display device.

A novel deep blue thermally activated delayed fluorescent material having high thermal stability and high ratio of thermally activated delayed fluorescent materials to photoluminescence quantum yield, and thus an organic light emitting diode display device having high luminescent efficiency is achieved.

DETAILED DESCRIPTION OF PREFERRED EMBODIMENTS

Figure 1:
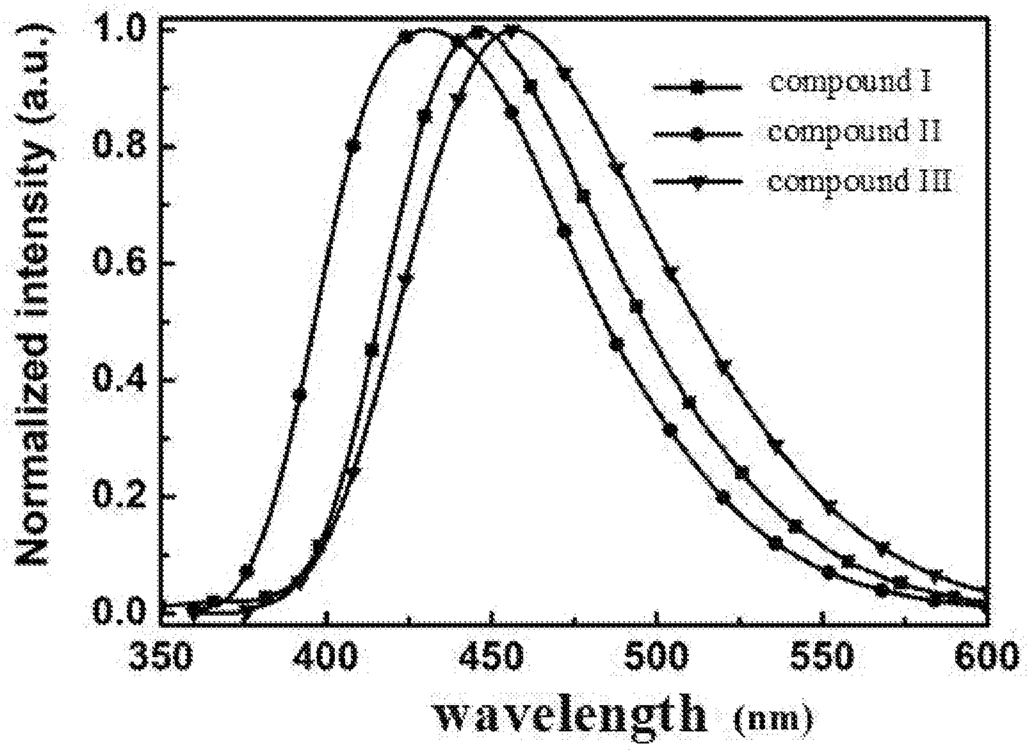
FIG. 1 is a photoluminescence spectrum of a thermally activated delayed fluorescent material in a toluene solution according to one embodiment of the present invention.

Generally, a thermally activated delayed fluorescent material has a molecular structure in which an electron donor and an electron acceptor are combined. In the embodiment of the present invention, organic thermally activated delayed fluorescence materials have a lowest single-triplet level difference (ΔEST) which is relatively less than ever before and a high photoluminescence quantum yield by adjusting a twist angle between the electron donor and the electron acceptor and charge transfer property, and thus an organic light emitting diode display device having high luminescent efficiency is achieved.

A thermally activated delayed fluorescent material, comprising a structural formula (I) as follows:

(I)

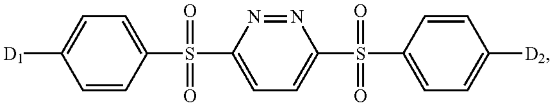

and D1 and D2 are different electron donors.

Specifically, D1 includes one of following chemical structural formulas:

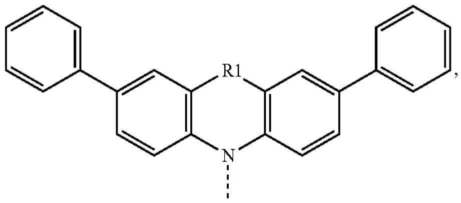, and R1 is selected one from an oxygen or a C1-C3 alkyl group;

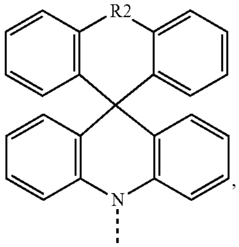, and the R2 selected one from a C1-C3 alkyl or a silane group;

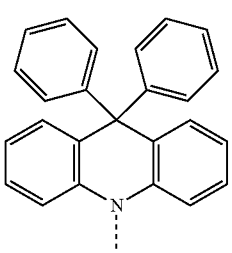, or 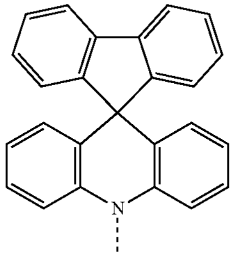.

Preferably, the D1 is selected one from the group consisting of

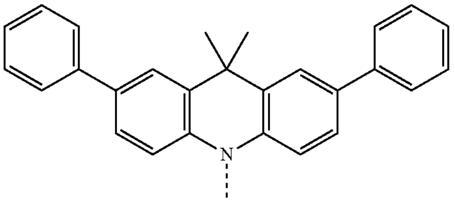,

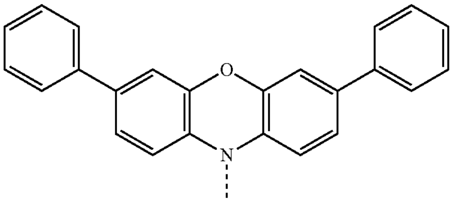,

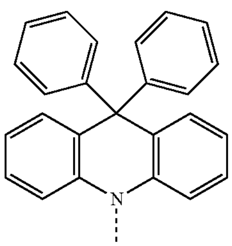, 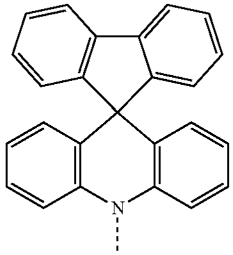,

-continued

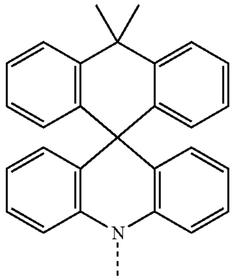, and 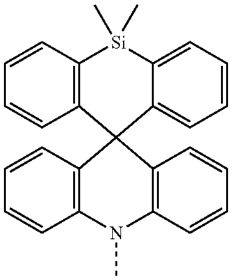.

Specifically, the D2 has a structural formula (I) as follows:

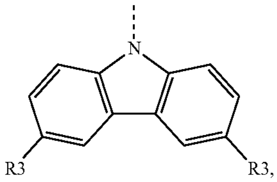

and the R3 is selected one from a hydrogen, a C1-C4 alkyl, an alkoxy, or an aryl. Preferably, the D2 is selected one from the group consisting of

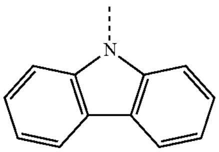, 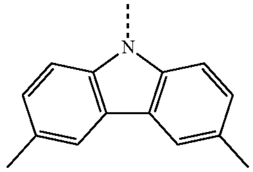,

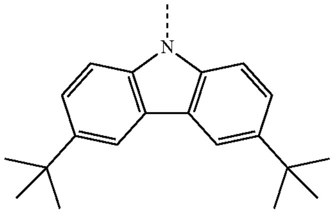,

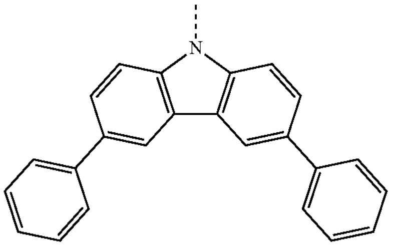, and

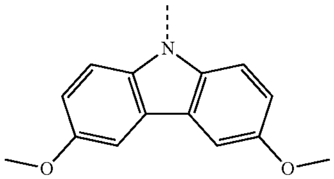.

The steps for synthesizing the thermally activated delayed fluorescent materials of various embodiments of the present invention are further described below.

A synthetic route for

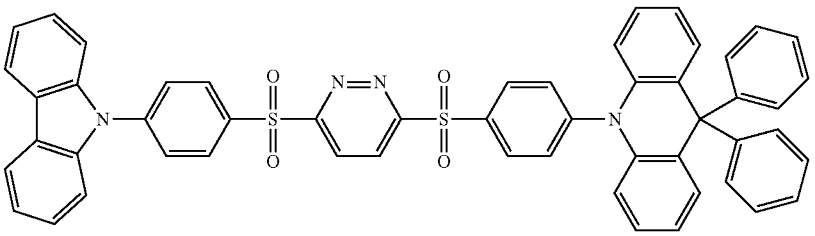

is described as follows:

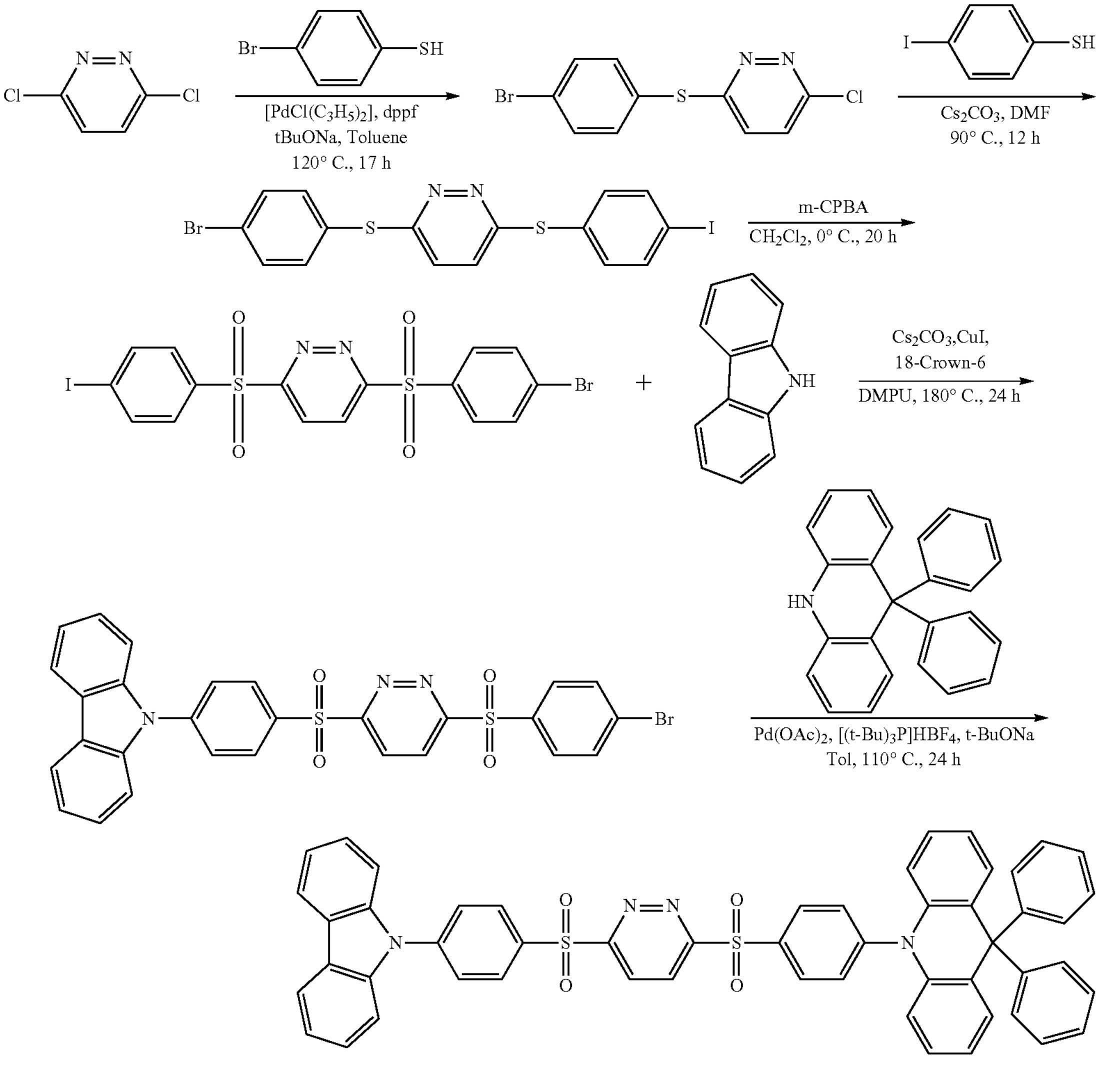

4-Bromothiophenol (2.36 g, 10 mmol), 3,6-dichloropyridazine (1.49 g, 10 mmol), $PdCl(CH_3H_5)_2$ (0.018 g, 0.05 mmol), 1,1'-Ferrocenediyl-bis(diphenylphosphine), dppf, (0.095 g, 0.2 mmol), and tBuONa (1.15 g, 12 mmol) are added to a 250 mL two-neck bottle and are vacuumed for three times. Then, 80 mL anhydrous, degassed toluene is added to the two-neck bottle under an argon atmosphere, and a reaction is performed at 120° C. for 17 hours, and reaction solution is cooled to room temperature and poured 200 mL into ice water. Then, the reaction solution is extracted with ethyl acetate (100 mL) for three times and combined with an organic phase, and the reaction solution is spun and dried. Next, the reaction solution is isolated and purified by column chromatography having a stationary phase of silica gel, in which a volume ratio of ethyl acetate to hexane is 1:9, to obtain a yellow oily liquid of 2.14 g, and a yield is 71%. Product identification data: $^1$H NMR (300 MHz, $CD_2Cl_2$, δ): 8.00 (d, J=7.5 Hz, 1H), 7.76 (m, 2H), 7.53 (m, 2H), 7.14 (d, J=7.5 Hz, 1H).

Next, 3-(4-bromothio)-6-chloropyridazine (2.1 g, 7 mmol), 4-iodobenzene-1-thiol (2.36 g, 10 mmol), cesium carbonate ($CS_2CO_3$, 3.26 g, 10 mmol) are added to a 100 mL two-neck bottle and are vacuumed for three times. Then, 50 mL anhydrous, degassed toluene is added to the two-neck bottle under an argon atmosphere, and a reaction is performed at 90° C. for 12 hours, and the reaction solution is cooled to room temperature and poured into 50 mL ice water. Then, the reaction solution is extracted with dichloromethane for three times and combined with an organic phase, and the reaction solution is spun and dried. Next, the reaction solution is isolated and purified by column chromatography having a stationary phase of silica gel, in which a volume ratio of ethyl acetate to hexane is 1:5, to obtain a yellow oily liquid of 2.8 g, and a yield is 80%. Product identification data: $^1$H NMR (300 MHz, $CD_2Cl_2$, δ): 7.73-7.80 (m, 6H), 7.53 (m, 2H), 7.13 (m, 2H).

3-(4-bromophenylthio)-6-(4-indodphenylsulfonyl)-pyridazine (2.5 g, 5 mmol) is added to the 100 mL two-neck bottle and is dissolved in the dichloromethane solution (20 mL), and then 0.1 M 70% m-CPBA in dichloromethane solution (200 mL, 20 mmol) is added at 0° C. and performed at 25° C. The reaction mixture is washed twice with saturated sodium thiosulfate ($Na_2S_2O_3$) and combined with an organic phase, and the reaction solution is spun, dried, and recrystallized with isopropanol to obtain a yellow solid of 2.4 g, and a yield is 85%. Product identification data: $^1$H NMR (300 MHz, $CD_2Cl_2$, δ): 8.36 (d, J=7.5 Hz, 2H), 8.12 (m, 2H), 7.92 (m, 2H), 7.69 (m, 2H), 7.57 (m, 2H).

Next, carbazole (0.67 g, 4 mmol), 3-(4-bromophenylsulfonyl)-6-(4-iodophenylsulfonyl)-pyridazine (2.26 g, 4 mmol), $Cs_2CO_3$ (2.31 g, 5 mmol), CuI (0.06 g, 0.3 mmol), and 18-Crown-6 ($(C_2H_4O)_6$, 26 mg, 0.1 mmol) are added to a 100 mL two-neck bottle and are vacuumed for three times. Then, 20 mL anhydrous, degassed 1,3-dimethyl-3,4,5,6-tetrahydro-2(1H)-pyrimidinone (DMPU) is added to the two-neck bottle under an argon atmosphere and performed at 180° C. for 24 hours. Next, the reaction solution is cooled to room temperature and poured into 200 mL ice water and filtered to obtain an off-white solid, which is then dissolved in dichloromethane, spun, and dried. Next, the reaction solution is isolated and purified by column chromatography having a stationary phase of silica gel, in which a volume ratio of dichloromethane to hexane is 1:3, to obtain a blue-white powder of 1.72 g, and a yield is 71%. Product identification data: $^1$H NMR (300 MHz, $CD_2Cl_2$, δ): 8.55 (m, 1H), 8.36 (d, J=7.5 Hz, 2H), 8.19 (m, 1H), 8.08 (m, 2H), 7.92-7.94 (m, 5H), 7.69 (m, 2H), 7.19-7.50 (m, 5H).

Next, 3-(4-bromophenylsulfonyl)-6-(4-carbazolephenylsulfonyl)-pyridazine (1.51 g, 2.5 mmol), 9,10-dihydro-9,9-diphenyl acridine (1.00 g, 3 mmol), palladium acetate (23 mg, 0.1 mmol), and tri-tert-butylphosphine tetrafluoroborate (0.09 g, 0.3 mmol) are added to a 100 mL two-neck bottle. Then, NaOt-Bu (0.30 g, 3 mmol) is added to the two-neck bottle in a glove box, and 40 mL anhydrous, degassed toluene is added to the two-neck bottle under an argon atmosphere, and a reaction is performed at 110° C. for 24 hours. Then, the reaction solution is cooled to room temperature and poured into 50 mL ice water, and the reaction solution is extracted with dichloromethane for three times and combined with an organic phase, and the reaction solution is spun and dried. Next, the reaction solution is isolated and purified by column chromatography having a stationary phase of silica gel, in which a volume ratio of dichloromethane to hexane is 1:1, to obtain a white powder of 1.07 g, and a yield is 50%. Finally, a final product is purified by using a sublimation instrument to obtain 0.6 g target compound (I)

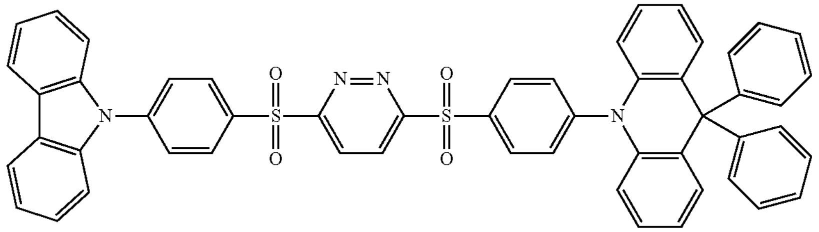 [SMILES: O=S(=O)(c1ccc(N2c3ccccc3C(c3ccccc3)(c3ccccc3)c3ccccc32)cc1)c1ccc(S(=O)(=O)c2ccc(-n3c4ccccc4c4ccccc43)cc2)nn1]

Product identification data: $^1$H NMR (300 MHz, $CD_2Cl_2$, δ): 8.55 (m, 1H), 8.36 (m, 2H), 8.19 (m, 1H), 8.08 (m, 2H), 7.94 (m, 2H), 7.66 (m, 2H), 7.50-7.58 (m, 4H), 7.19-7.26 (m, 20H), 6.95 (m, 2H).

A synthetic route for

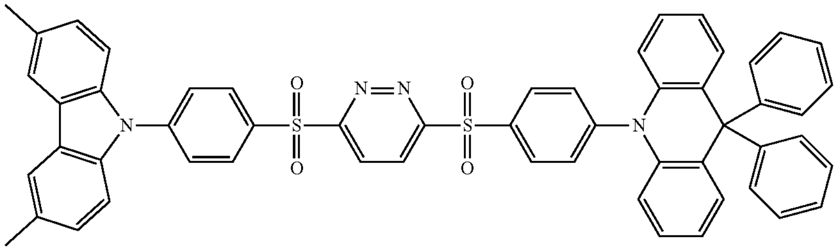 [SMILES: Cc1ccc2c(c1)c1cc(C)ccc1n2-c1ccc(S(=O)(=O)c2ccc(S(=O)(=O)c3ccc(N4c5ccccc5C(c5ccccc5)(c5ccccc5)c5ccccc54)cc3)nn2)cc1]

is described as follows:

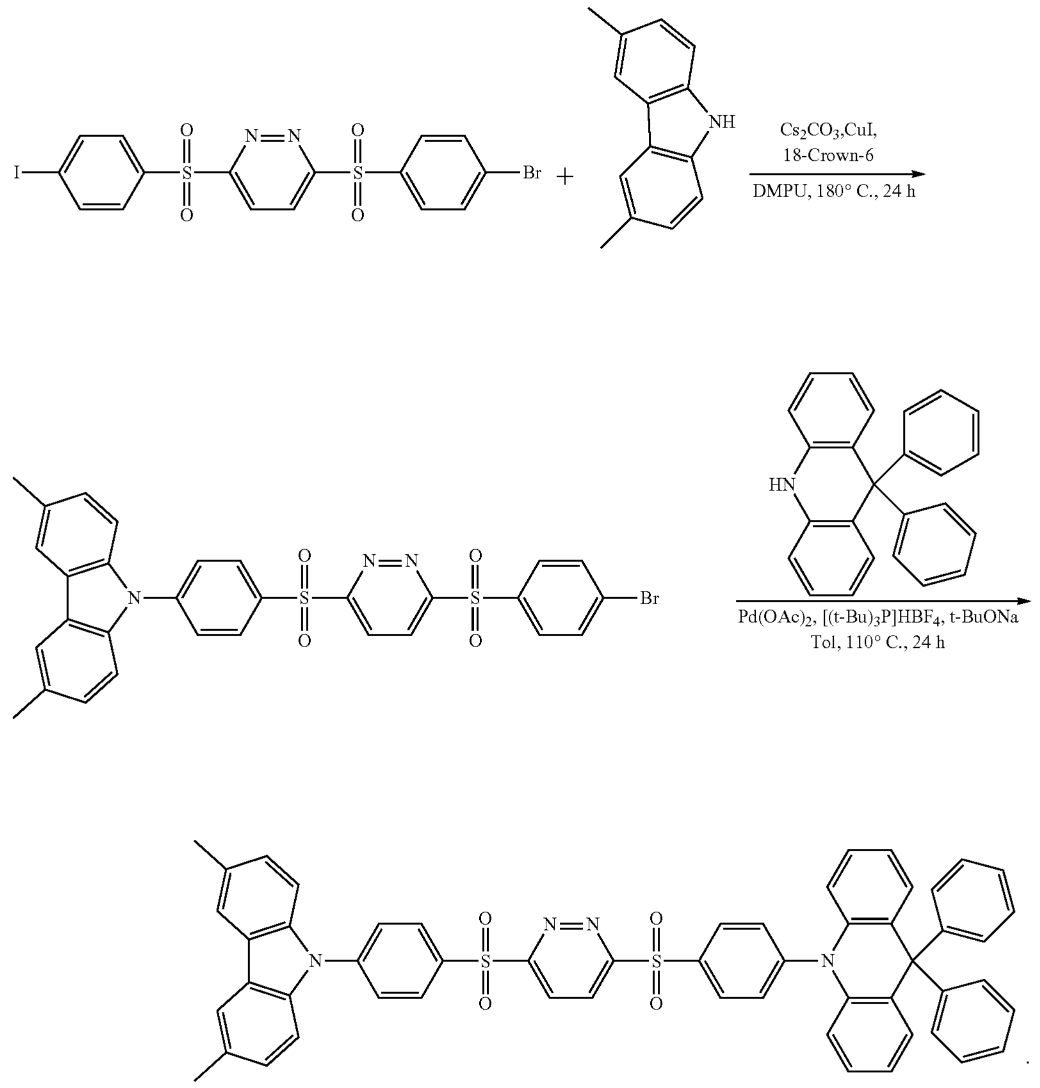

3,6-dimethylcarbazole (1.95 g, 10 mmol), 3-(4-bromophenylsulfonyl)-6-(4-iodophenylsulfonyl)-pyridazine (5.65 g, 10 mmol), $Cs_2CO_3$ (2.31 g, 12 mmol), CuI (0.11 g, 0.6 mmol), and 18-Crown-6 ($(C_2H_4O)_6$, 52 mg, 0.2 mmol) are added to a 100 mL two-neck bottle and are vacuumed for three times. Then, 50 mL anhydrous, degassed 1,3-dimethyl-3,4,5,6-tetrahydro-2(1H)-pyrimidinone (DMPU) is added to the two-neck bottle under an argon atmosphere and performed at 180° C. for 24 hours. Next, the reaction solution is cooled to room temperature and poured into 200 mL ice water and filtered to obtain an off-white solid, which is then dissolved in dichloromethane, spun, and dried. Next, the reaction solution is isolated and purified by column chromatography having a stationary phase of silica gel, in which a volume ratio of dichloromethane to hexane is 1:3, to obtain a blue-white powder of 4.1 g, and a yield is 65%. Product identification data: $^1$H NMR (300 MHz, $CD_2Cl_2$, δ): 8.80 (s, 1H), 8.36 (d, J=7.5 Hz, 2H), 8.03-8.08 (m, 3H), 7.89-7.94 (m, 5H), 7.69 (m, 2H), 7.53 (m, 1H), 7.38 (m, 1H), 6.96 (m, 1H), 2.46 (s, 6H).

Next, 3-(4-bromophenylsulfonyl)-6-(4-(3, 6-dimethylcarbazole) phenylsulfonyl)-pyridazine (3.16 g, 5 mmol), 9,10-dihydro-9,9-diphenyl acridine (1.00 g, 6 mmol), palladium acetate (45 mg, 0.2 mmol), and tri-tert-butylphosphine tetrafluoroborate (0.17 g, 0.6 mmol) are added to a 100 mL two-neck bottle. Then, NaOt-Bu (0.58 g, 6 mmol) is added to the two-neck bottle in a glove box, and 50 mL anhydrous, degassed toluene is added to the two-neck bottle under an argon atmosphere, and a reaction is performed at 110° C. for 24 hours. Then, the reaction solution is cooled to room temperature and poured into 50 mL ice water, and the reaction solution is extracted with dichloromethane for three times and combined with an organic phase, and the reaction solution is spun and dried. Next, the reaction solution is isolated and purified by column chromatography having a stationary phase of silica gel, in which a volume ratio of dichloromethane to hexane is 1:1, to obtain a blue-white powder of 2.1 g, and a yield is 47%. Finally, a final product is purified by using a sublimation instrument to obtain 1.2 g target compound (II)

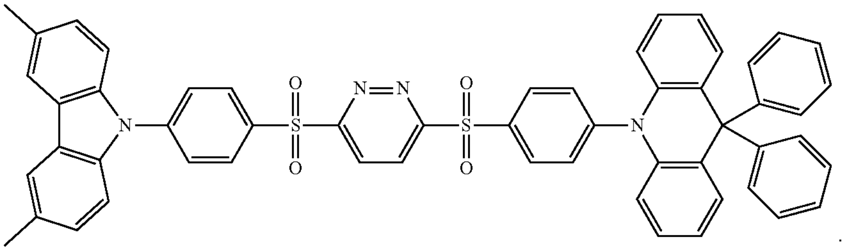 [SMILES: Cc1ccc2c(c1)c1cc(C)ccc1n2-c1ccc(S(=O)(=O)c2ccc(S(=O)(=O)c3ccc(N4c5ccccc5C(c5ccccc5)(c5ccccc5)c5ccccc54)cc3)nn2)cc1]
Product identification data: $^1$H NMR (300 MHz, $CD_2Cl_2$, δ): 8.80 (s, 1H), 8.36 (d, J=7.5 Hz, 2H), 8.03-8.08 (m, 3H), 7.89-7.94 (m, 3H), 7.66 (m, 2H), 7.53 (m, 3H), 7.38 (m, 1H), 6.96-7.19 (m, 19H), 2.46 (s, 6H).
A synthetic route for
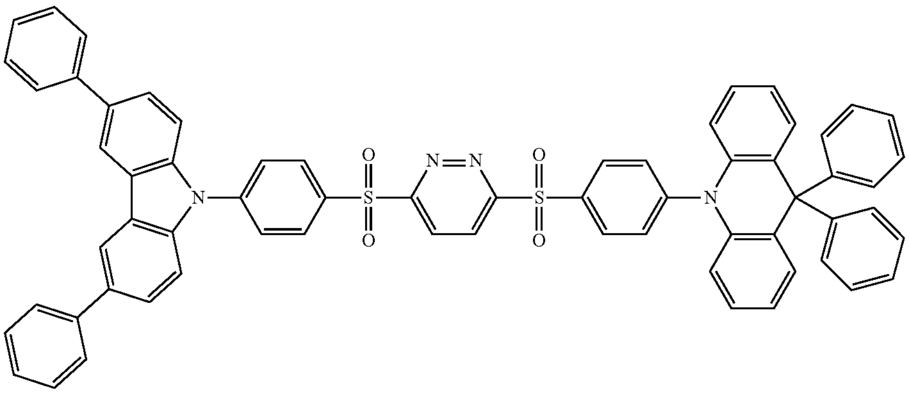 [SMILES: O=S(=O)(c1ccc(N2c3ccccc3C(c3ccccc3)(c3ccccc3)c3ccccc32)cc1)c1ccc(S(=O)(=O)c2ccc(-n3c4ccc(-c5ccccc5)cc4c4cc(-c5ccccc5)ccc43)cc2)nn1]
is described as follows:
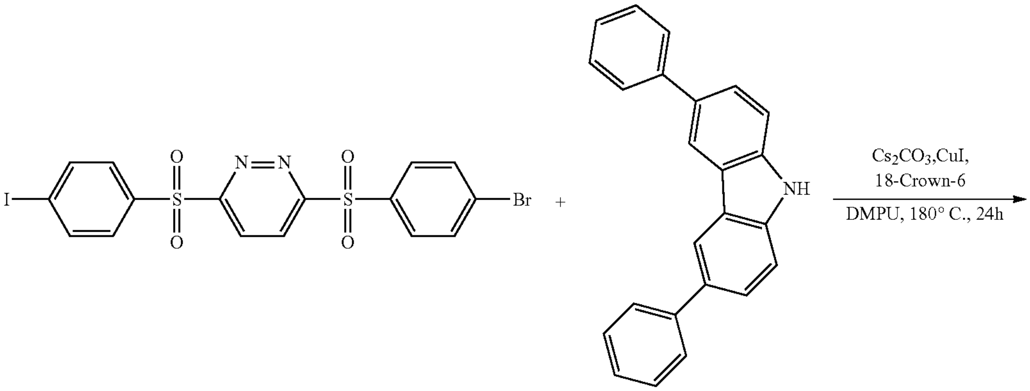

-continued

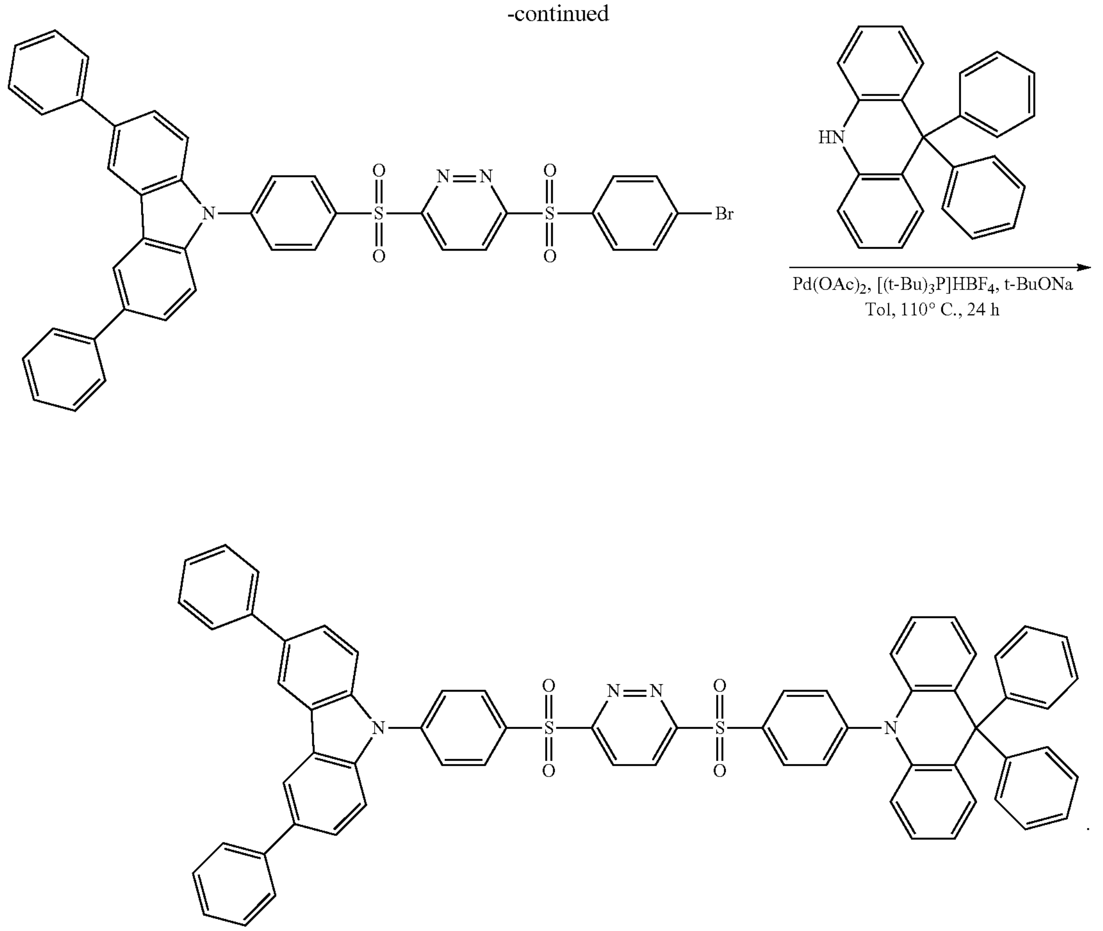

3,6-diphenylcarbazole (3.19 g, 10 mmol), 3-(4-bromophenylsulfonyl)-6-(4-iodophenylsulfonyl)-pyridazine (5.65 g, 10 mmol), $Cs_2CO_3$ (2.31 g, 12 mmol), CuI (0.11 g, 0.6 mmol), and 18-Crown-6 ($(C_2H_4O)_6$, 52 mg, 0.2 mmol) are added to a 100 mL two-neck bottle and are vacuumed for three times. Then, 50 mL anhydrous, degassed 1,3-dimethyl-3,4,5,6-tetrahydro-2(1H)-pyrimidinone (DMPU) is added to the two-neck bottle under an argon atmosphere and performed at 180° C. for 24 hours. Next, the reaction solution is cooled to room temperature and poured into 200 mL ice water and filtered to obtain an off-white solid, which is then dissolved in dichloromethane, spun, and dried. Next, the reaction solution is isolated and purified by column chromatography having a stationary phase of silica gel, in which a volume ratio of dichloromethane to hexane is 1:3, to obtain a blue-white powder of 4.77 g, and a yield is 63%. Product identification data: $^1H$ NMR (300 MHz, $CD_2Cl_2$, δ): 8.36 (d, J=7.5 Hz, 2H), 8.30 (m, 1H), 8.08-8.13 (m, 3H), 7.89-7.99 (m, 7H), 7.69-7.77 (m, 7H), 7.41-7.49 (m, 6H).

Next, 3-(4-bromophenylsulfonyl)-6-(4-(3, 6-dimethylcarbazole) phenylsulfonyl)-pyridazine (3.78 g, 5 mmol), 9,10-dihydro-9,9-diphenyl acridine (1.00 g, 6 mmol), palladium acetate (45 mg, 0.2 mmol), and tri-tert-butylphosphine tetrafluoroborate (0.17 g, 0.6 mmol) are added to a 100 mL two-neck bottle. Then, NaOt-Bu (0.58 g, 6 mmol) is added to the two-neck bottle in a glove box, and 50 mL anhydrous, degassed toluene is added to the two-neck bottle under an argon atmosphere, and a reaction is performed at 110° C. for 24 hours. Then, the reaction solution is cooled to room temperature and poured into 50 mL ice water, and the reaction solution is extracted with dichloromethane for three times and combined with an organic phase, and the reaction solution is spun and dried. Next, the reaction solution is isolated and purified by column chromatography having a stationary phase of silica gel, in which a volume ratio of dichloromethane to hexane is 1:1, to obtain a white powder of 2.0 g, and a yield is 40%. Finally, a final product is purified by using a sublimation instrument to obtain 1.1 g target compound (III)

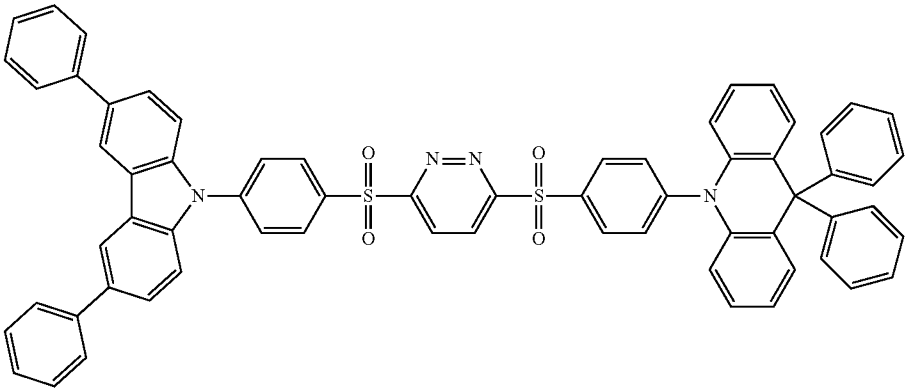 [SMILES: O=S(=O)(c1ccc(N2c3ccccc3C(c3ccccc3)(c3ccccc3)c3ccccc32)cc1)c1ccc(S(=O)(=O)c2ccc(-n3c4ccc(-c5ccccc5)cc4c4cc(-c5ccccc5)ccc43)cc2)nn1]

Product identification data: $^1H$ NMR (300 MHz, $CD_2Cl_2$, δ): 8.36 (d, J=7.5 Hz, 2H), 8.30 (m, 1H), 8.08-8.13 (m, 3H), 7.89-7.94 (m, 5H), 7.75-7.77 (m, 5H), 7.66 (m, 2H), 7.41-7.53 (m, 8H), 7.17-7.40 (m, 16H), 6.95 (m, 2H).

The lowest singlet energy level (S1) and the lowest triplet energy level (T1) of the target compound I, the target compound II, and the target compound III, and the electrochemical energy levels are as shown in Table 1 below:

TABLE 1

| | PL Peak (nm) | $S_1$ (eV) | $T_1$ (eV) | $\Delta E_{ST}$ (eV) | HOMO (eV) | LUMO (eV) |
|---|---|---|---|---|---|---|
| Target compound (I) | 449 | 2.76 | 2.73 | 0.03 | −5.58 | −2.30 |
| Target compound (II) | 431 | 2.88 | 2.80 | 0.08 | −5.64 | −2.31 |
| Target compound (III) | 456 | 2.72 | 2.66 | 0.04 | −5.53 | −2.30 |

Referring to FIG. 1, it is a photoluminescence spectrum of a thermally activated delayed fluorescent material (compound I, compound II, and compound III) in a toluene solution according to one embodiment of the present invention.

In another embodiment, an organic light emitting diode display device includes an anode, a cathode, and an organic functional layer disposed between the anode and the cathode. The organic functional layer incudes a thermally activated delayed fluorescent material, and the thermally activated delayed fluorescent material includes a structural formula (I) as follows:

(I)

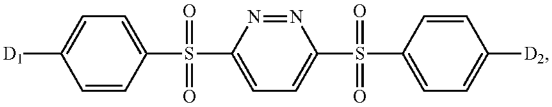

and the D1 is selected one from the group consisting of

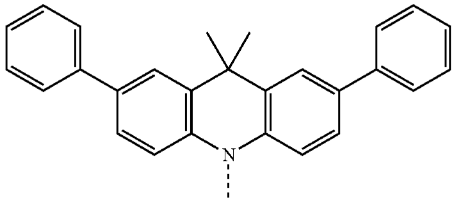

,

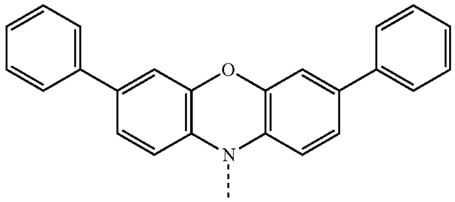

,

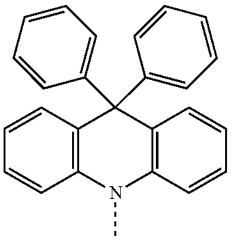

,

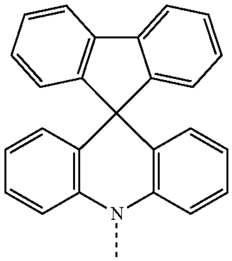

,

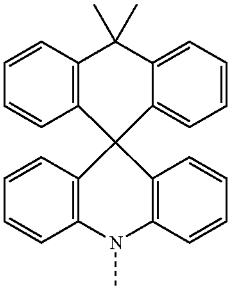

, and

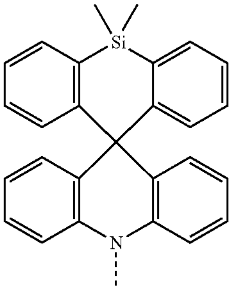

;

and D2 is selected one from the group consisting of

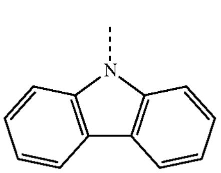

,

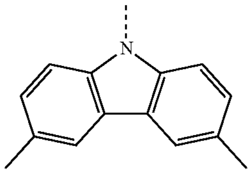

,

-continued

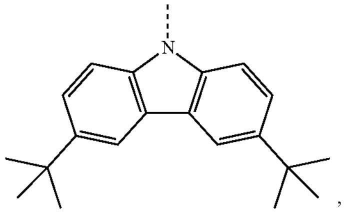

,

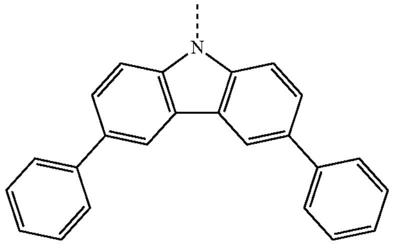

, and

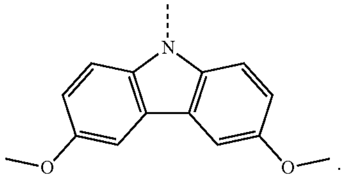

.

Specifically, the thermally activated delayed fluorescent material is a fluorescent host material or an electron transporting material used in the organic light emitting diode display device.

Figure 2:
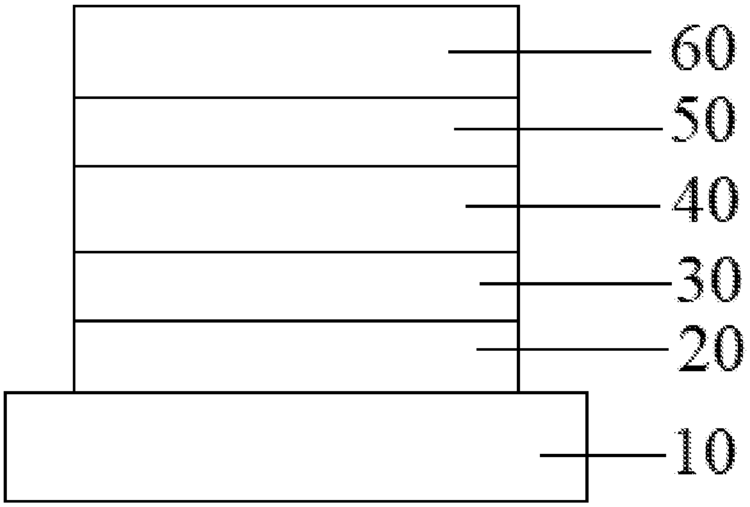
FIG. 2 is a schematic view of an organic light emitting diode display device using a thermally activated delayed fluorescent material as a light emitting layer according to one embodiment of the present invention.

Referring to FIG. 2, it is a schematic view of an organic light emitting diode display device using a thermally activated delayed fluorescent material as a light emitting layer according to one embodiment of the present invention. The organic light-emitting diode device includes a glass substrate and a conductive glass layer 10 made of indium tin oxide (ITO), a hole injection layer 20, a hole transport layer 30, a light emitting layer 40, an electron transport layer 50, and a cathode layer 60. Specifically, the hole injection layer 20 is made of poly 3,4-ethylenedioxythiophene and polystyrene sulfonate. The electron transport layer 50 is made of 1,3, 5-tris(3-(3-pyridyl)phenyl)benzene. The cathode layer 60 is made of lithium fluoride and aluminum. The organic light emitting diode display device can be achieved by a well-known method in the art, so it will not be described again.

Furthermore, current, brightness, and voltage characteristics of organic light emitting diode display device are achieved by a Keithley source measurement system (Keithley 2400 Sourcemeter, Keithley 2000 Currentmeter) with a silicon photodiode which is calibrated. An electroluminescence spectrum is measured by the French JY SPEX CCD3000 spectrometer, and all measurements are performed at room temperature in the atmosphere.

The organic light emitting diode display devices (device I, device II, and device III) use target compound I, target compound II, and target compound III, respectively, and their performance data are shown in Table 2 below:

TABLE 2

| Device | maximum brightness (cd/A) | (CIEx, CIEy) | Maximum external quantum efficiency (%) |
|---|---|---|---|
| organic light emitting diode display device I | 14.3 | (0.13, 0.13) | 16.9% |
| organic light emitting diode display device II | 12.6 | (0.13, 0.09) | 14.8% |
| organic light emitting diode display device III | 16.3 | (0.13, 0.17) | 11.8% |

In the embodiment of the present invention, the deep blue high thermally activated delayed fluorescent material has a high ratio of thermally activated delayed fluorescent material to photoluminescence quantum yield, thereby an organic light emitting diode display device having high luminescent efficiency high is achieved.

In the above, the present application has been described in the above preferred embodiments, but the preferred embodiments are not intended to limit the scope of the invention, and a person skilled in the art may make various modifications without departing from the spirit and scope of the application. The scope of the present application is determined by claims.

What is claimed is:

1. A thermally activated delayed fluorescent material, comprising a structural formula (I) as follows:

(I)

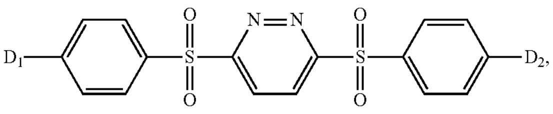

wherein D1 and D2 are different electron donors.

2. The thermally activated delayed fluorescent material according to claim 1, wherein the D1 comprises one of following chemical structural formulas:

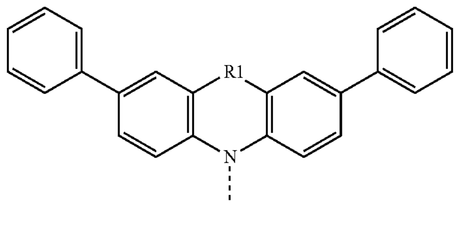

, wherein R1 is selected one from an oxygen or a C1-C3 alkyl group;

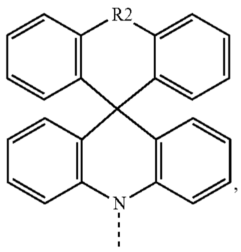

, wherein the R2 selected one from a C1-C3 alkyl or a silane group;

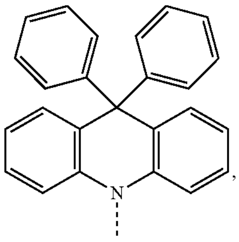, or 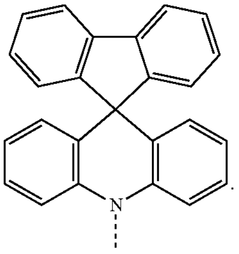.

3. The thermally activated delayed fluorescent material according to claim 1, wherein the D1 is selected one from the group consisting of

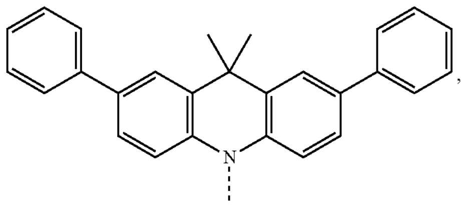,

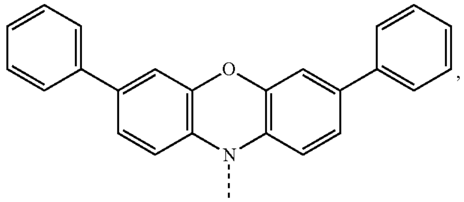,

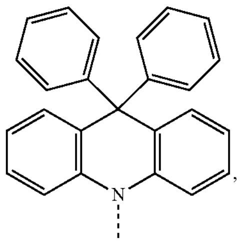, 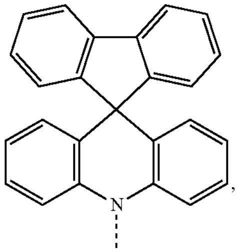,

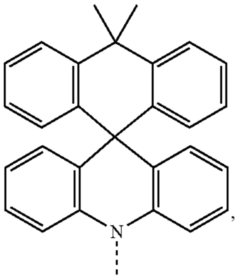, and 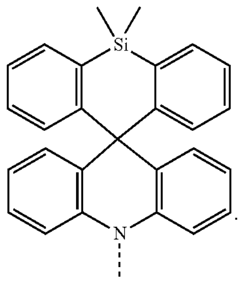.

4. The thermally activated delayed fluorescent material according to claim 1, wherein the D2 has a structural formula (I) as follows:

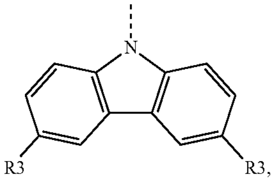

wherein the R3 is selected one from a hydrogen, a C1-C4 alkyl, an alkoxy, or an aryl.

5. The thermally activated delayed fluorescent material according to claim 4, wherein the D2 is selected one from the group consisting of

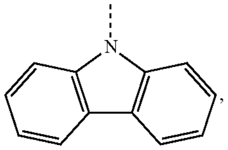, 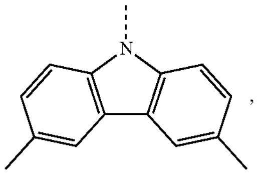,

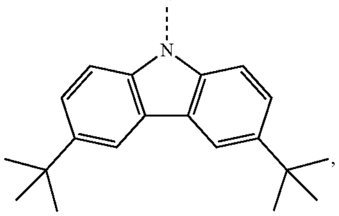,

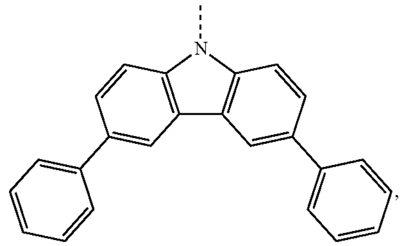, and

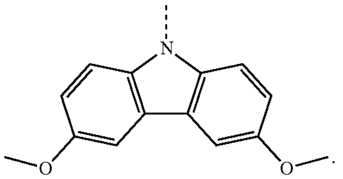.

6. An organic light emitting diode display device, comprising an anode, a cathode, and an organic functional layer disposed between the anode and the cathode, wherein the organic functional layer comprises a thermally activated delayed fluorescent material, and the thermally activated delayed fluorescent material comprises a structural formula (I) as follows:

(I)

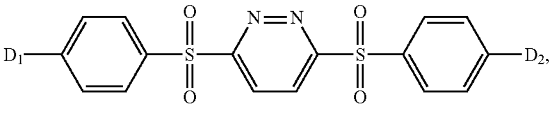

wherein the D1 is selected one from the group consisting of

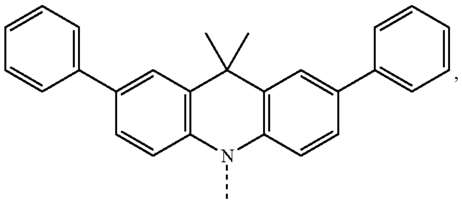

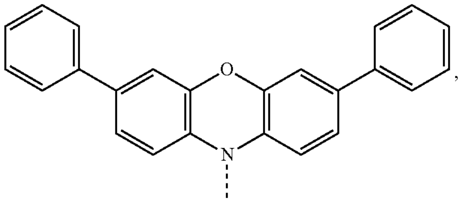

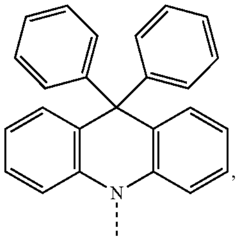

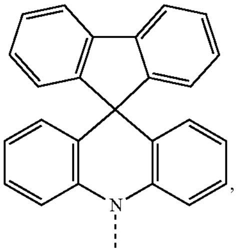

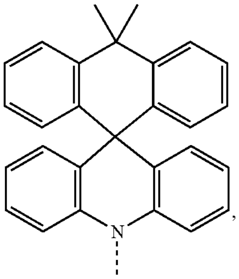

and

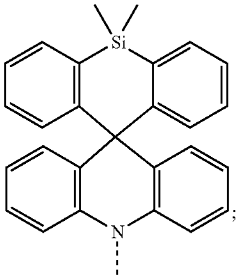

and

D2 is selected one from the group consisting of

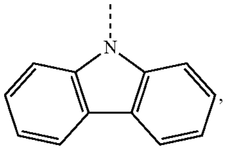

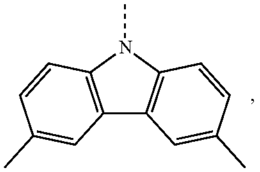

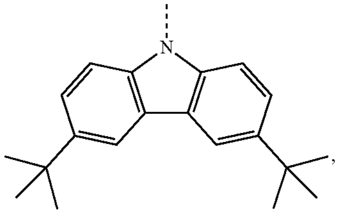

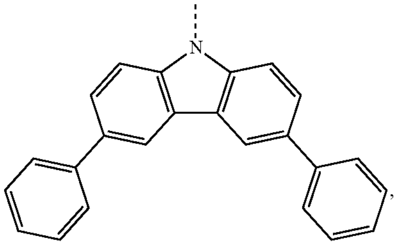

and

-continued

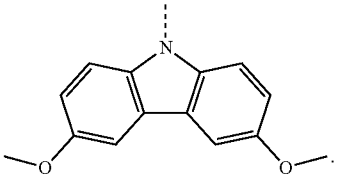

7. The organic light emitting diode display device according to claim 6, wherein the thermally activated delayed fluorescent material is a fluorescent host material used in the organic light emitting diode display device.

8. The organic light emitting diode display device according to claim 6, wherein the thermally activated delayed fluorescent material is an electron transporting material used in the organic light emitting diode display device.

9. A thermally activated delayed fluorescent material, comprising a structural formula (I) as follows:

(I)

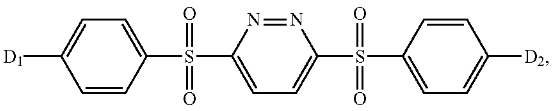

wherein D1 and D2 are different electron donors, and the D1 comprises one of following chemical structural formulas:

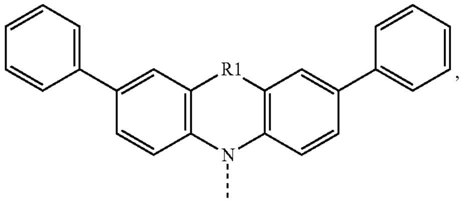

wherein R1 is selected one from an oxygen or a C1-C3 alkyl group;

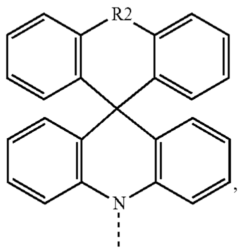

wherein the R2 selected one from a C1-C3 alkyl or a silane group;

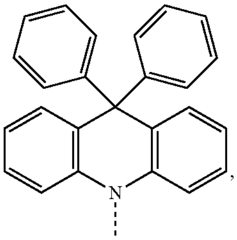

or

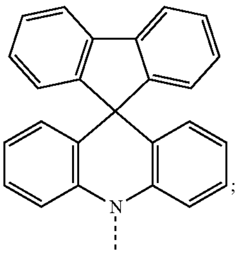

;

and the D2 has a structural formula (I) as follows:

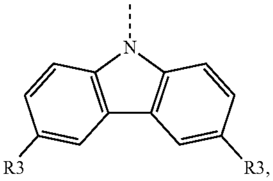

wherein the R3 is selected one from a hydrogen, a C1-C4 alkyl, an alkoxy, or an aryl.

10. The thermally activated delayed fluorescent material according to claim 9, wherein the D1 is selected one from the group consisting of

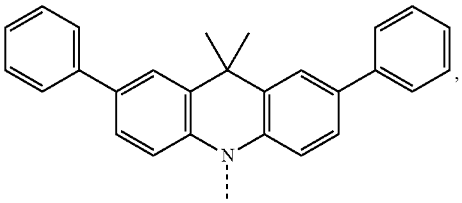

,

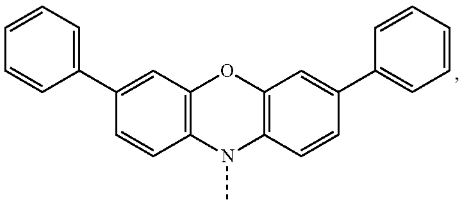

,

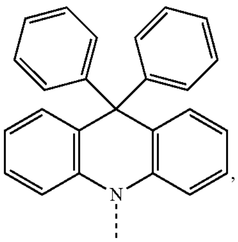

,

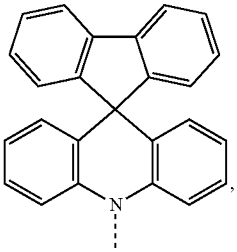

,

-continued

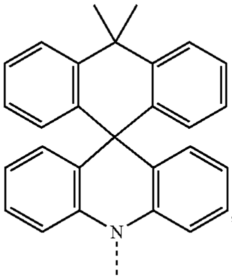

, and

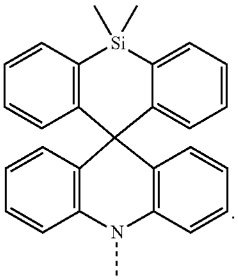

.

11. The thermally activated delayed fluorescent material according to claim 9, wherein the D2 is selected one from the group consisting of

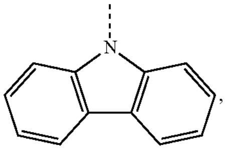

,

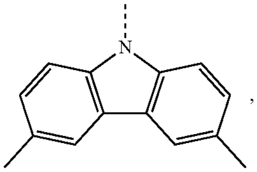

,

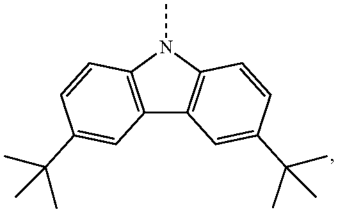

,

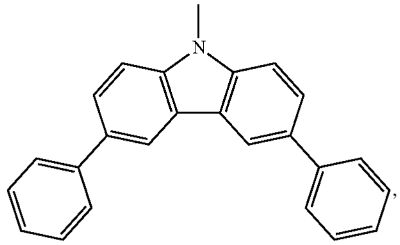

, and

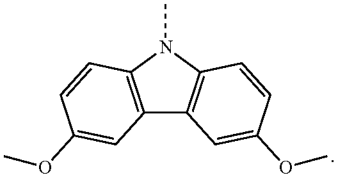

.

12. The thermally activated delayed fluorescent material according to claim 9, wherein the organic functional layer comprises a thermally activated delayed fluorescent material.

13. The thermally activated delayed fluorescent material according to claim 9, wherein the thermally activated delayed fluorescent material is a fluorescent host material used in the organic light emitting diode display device.

14. The thermally activated delayed fluorescent material according to claim 9, wherein the thermally activated delayed fluorescent material is an electron transporting material used in the organic light emitting diode display device.

* * * * *